(12) United States Patent
Moolman et al.

(10) Patent No.: US 7,700,335 B2
(45) Date of Patent: Apr. 20, 2010

(54) STABILIZATION OF ENZYMES IN AN EMULSION BY CROSS-LINKING

(75) Inventors: Francis Dean Moolman, Pretoria (ZA); Dean Brady, Johannesburg (ZA); Avashnee Chetty, Johannesburg (ZA); Heidi Rolfes, Pretoria (ZA); Justin Jordaan, Geriston (ZA)

(73) Assignee: CSIR, Pretoria (ZA)

( * ) Notice: Subject to any disclaimer, the term of this patent is extended or adjusted under 35 U.S.C. 154(b) by 693 days.

(21) Appl. No.: 10/586,894

(22) PCT Filed: Jan. 27, 2005

(86) PCT No.: PCT/IB2005/000192

§ 371 (c)(1), (2), (4) Date: Jul. 21, 2006

(87) PCT Pub. No.: WO2005/080561

PCT Pub. Date: Sep. 1, 2005

(65) Prior Publication Data

US 2008/0213858 A1    Sep. 4, 2008

(30) Foreign Application Priority Data

Jan. 28, 2004    (ZA) .................................. 04/0685

(51) Int. Cl.
  *C12N 9/96* (2006.01)
  *C12N 9/16* (2006.01)
  *C12N 9/20* (2006.01)
  *B01F 3/08* (2006.01)

(52) U.S. Cl. .................. 435/188; 435/196; 435/198; 516/21; 516/53

(58) Field of Classification Search ............. 435/188, 435/196, 198; 516/21, 53
See application file for complete search history.

(56) References Cited

U.S. PATENT DOCUMENTS 4,492,684 A  *  1/1985  Goosen et al. .............. 424/486

(Continued)

FOREIGN PATENT DOCUMENTS

EP       1 088 887 A1     4/2001

(Continued)

OTHER PUBLICATIONS

Abe et al., "Surfactant-chymotrypsin complex as a novel biocatalyst in organic media," Journal of Fermentation and Bioengineering 83(6):555-560, 1997.*

(Continued)

*Primary Examiner*—Karen Cochrane Carlson
*Assistant Examiner*—Rosanne Kosson
(74) *Attorney, Agent, or Firm*—Knobbe Martens Olson & Bear LLP (57) ABSTRACT

A process for producing enzymes structures includes providing an emulsion of droplets of a first liquid phase dispersed in a second liquid phase. The one liquid phase is a hydrophilic phase, while the other liquid phase is a hydrophobic phase which is immiscible with the hydrophilic phase. Enzyme molecules are located at or within interfacial boundaries of the droplets and the second liquid phase. The enzyme molecules of the respective droplets are cross-linked so that individual enzyme structures, which are stable and in which the enzymes are immobilized with a majority of active sites of the enzymes being orientated either internally or externally, are formed from individual droplets.

18 Claims, 4 Drawing Sheets

Lipase spheres obtained according to Example 2.

U.S. PATENT DOCUMENTS

| | | | |
|---|---|---|---|
| 4,671,954 A * | 6/1987 | Goldberg et al. | 424/1.37 |
| 5,279,847 A | 1/1994 | Okonogi et al. | |
| 6,303,150 B1 | 10/2001 | Perrier et al. | |
| 6,343,225 B1 * | 1/2002 | Clark, Jr. | 600/347 |

FOREIGN PATENT DOCUMENTS

WO    WO 01/62280 A2    8/2001

OTHER PUBLICATIONS

Bachtsi, A. et al. (1995) "An experimental investigation of enzyme release from poly(vinyl alcohol) crosslinked microspheres" *J. Microencapsulation* 12:23-35.

Betancor, L. et al. (2003) "Preparation of a stable biocatalyst of bovine liver catalase using immobilization and postimmobilization techniques" *Biotechnol. Prog.* 19:763-767.

Bezemer, J.M. et al. (2000) "Microspheres for protein delivery prepared from amphiphilic multiblock copolymers 1. Influence of preparation techniques on particle characteristics and protein delivery" *J. Controlled Release* 67:233-248.

Higashi, S. et al. (2000) "Hepatic arterial injection chemotherapy for hepatocellular carcinoma with epirubicin aqueous solution as numerous vesicles in iodinated poppy-seed oil microdroplets: clinical application of water-in-oil-in-water emulsion prepared using a membrane emulsification technique" *Adv. Drug Delivery Rev.* 45:57-64.

Lee, S. et al. (2000) "Preparation and some properties of water-insoluble, whey protein-based microcapsules" *J. Microencapsulation* 17:19-44.

Lopez-Serrano, P. (2002) "Cross-linked enzyme aggregates with enhanced activity: application to lipases" *Biotechnol. Lett.* 24:1379-1383.

Nakashima, T. et al. (2000) "Particle control of emulsion by membrane emulsification and its applications" *Adv. Drug Delivery Rev.* 45:47-56.

Sharma, R. et al. (2001) "Production, purification, characterization, and applications of lipases" *Biotechnol. Adv.* 19:627-662.

Tischer, W. et al. (1999) "Immobilized enzymes: crystals or carriers?" *Tibtech* 17:326-335.

Vorderwulbecke, T. et al. (1992) "Comparison of lipases by different assays" *Enzyme Microb. Technol.* 14:631-639.

Walde, P. et al. (2001) "Enzymes inside lipid vesicles: preparation, reactivity and applications" *Biomolecular Eng.* 18:143-177.

\* cited by examiner

Figure 3. Lipase spheres obtained according to Example 2.

FIG 3

Figure 4. Particle size distribution of lipase spheres according to Example 2.

FIG 4

STABILIZATION OF ENZYMES IN AN EMULSION BY CROSS-LINKING

RELATED APPLICATIONS

This application is a US National Phase of International Application No. PCT/IB2005/000192, filed Jan. 27, 2005, designating the US and published in English on Sep. 1, 2005 as WO 2005/080561, which claims the benefit of South African Patent Application No. 2004/0685, filed Jan. 28, 2004.

FIELD OF THE INVENTION

THIS INVENTION relates to the stabilization of enzymes. More particularly, it relates to a process for producing stabilized enzyme structures, to stabilized enzyme structures, and to the use of such stabilized enzyme structures.

DESCRIPTION OF THE RELATED ART

Enzymes are commonly required as catalysts in various industries, such as in chemical, pharmaceutical and cosmetic industries. However, unlike chemical catalysts, enzymes have limited application and shelf life due to their instability. Enzymes are extremely temperature and pH dependant, making their use in many processes difficult. In addition, soluble enzymes cannot be easily recovered from aqueous media, and enzyme activity generally decreases during storage or processing, limiting the application of enzymes as catalysts in chemical processing.

Commercial application of enzymes as catalysts can be enhanced by enzyme immobilization, which provides the dual advantages of increasing enzyme stability by making the enzymes more rigid (by immobilizing them on or in a solid phase), and increasing the overall size of the catalyst, thereby making recovery simpler.

Immobilization of enzymes onto solid supports is therefore commonly practiced with the aim of stabilizing the enzymes and reducing costs by making them recyclable. However, immobilized enzymes display limitations, the most important being reduced enzyme activity per unit reactor volume due to only a small fraction of the immobilized volume constituting the active catalyst (enzyme). The Applicant is also aware of self-supported immobilized enzymes in the form of cross-linked enzyme crystals (CLEC) and cross-linked enzyme agglomerates (CLEA). Claims to increased specific activity have been made for both of these. In addition, CLEC and CLEA cross-linked enzymes are stable in reaction media, and can be easily separated and recycled. CLEA appears to provide a less expensive and more efficient method compared to CLEC where time-consuming crystallization protocols are required. However, both CLEC and CLEA are limiting in that some active sites of the enzymes are not exposed, and hence processes utilizing either CLEA or CLEC would require excess enzyme catalyst (with an associated increased cost) for a particular function, to compensate for this. In addition these processes do not have easy control over particle size and morphology over a large range of particle sizes.

SUMMARY OF THE INVENTION

It is thus an object of this invention to provide a process for producing stabilized enzyme structures suitable for use as a catalyst, whereby these drawbacks are at least reduced.

Thus, according to a first aspect of the invention, there is provided a process for producing enzyme structures, which process includes providing an emulsion of droplets of a first liquid phase dispersed in a second liquid phase, with the one liquid phase being a hydrophilic phase and the other liquid phase being a hydrophobic phase which is immiscible with the hydrophilic phase, and with enzyme molecules being located at or within interfacial boundaries of the droplets and the second liquid phase; and cross-linking the enzyme molecules of the respective droplets so that individual enzyme structures, which are stable and in which the enzymes are immobilized with a majority of active sites of the enzymes being orientated either internally or externally, are formed from individual droplets.

Since, in an emulsion, the droplets of the immiscible first liquid phase are normally spherical, the structures will thus normally be of hollow spherical form, with the insides or interiors of the spherical structures being either empty or filled. In other words, each enzyme structure comprises a spherical wall of cross-linked immobilized enzyme molecules, and a hollow centre, core or interior which can either be empty or contain a liquid, i.e. be filled, as hereinafter described.

In one embodiment of the invention, the individual structures may have openings so that the liquid phases can pass in or out of the structures. However, in another embodiment of the invention, the structures may be liquid impervious, ie they may be in the form of capsules, with the first liquid phase then being trapped inside the capsules ie filling the hollow cores of the capsules. If such stabilized enzyme capsules are then used in a liquid reaction system, eg to catalyze the reaction system, they can easily be separated from the other components of the reaction system, eg by flotation, by selecting a first liquid phase having an appropriate density. However, when used in such a system, they need not necessarily only be separated by flotation since the fact that the stabilized enzyme structures are self-supporting, means that they can easily be separated from the other components in the reaction system and recycled or re-used.

Enzyme molecules often contain both hydrophilic and hydrophobic ends or faces. When such enzymes are used, collection and/or orientation thereof at the interfacial boundaries of the droplets and the second liquid phase, will be enhanced or ensured. Modifications may be made to native enzymes to enhance such properties. Thus, an additive for modifying the hydrophobicity and/or charge of the enzyme may be added to the hydrophilic phase and/or to the hydrophobic phase and/or to the emulsion. Examples of additives or modifiers that can be used for this purpose include specific amino acids; amino compounds; proteins; long chain hydrocarbon aldehydes; and other modifiers which bind covalently or otherwise to the enzymes.

While the enzyme can be selected from enzyme classes such as Esterases, Proteases, Nitrilases, Nitrile hydratases, Oxynitrilases, Epoxide hydrolases, Halohydrin dehalogenases, Polyphenoloxidases (eg laccase), Penicillin amidases, Amino acylases, Ureases, Uricases, Lysozymes Asparaginases, Elastases, it is preferably lipase.

The lipase can be chosen from microbial, animal, or plant sources, including any one of the following: *Pseudomonas cepacia* lipase, *Pseudomonas fluorescens* lipase, *Pseudomonas alcaligenes* lipase *Candida rugosa* lipase, *Candida antarctica* lipase A, *Candida antarctica* lipase B, *Candida utilis* lipase, *Thermomyces lanuginosus* lipase, *Rhizomucor miehei* lipase, *Aspergillus niger* lipase, *Aspergillus oryzae* lipase, *Penicillium* sp lipase, *Mucor javanicus* lipase, *Mucor miehei* lipase, *Rhizopus arrhizus* lipase, *Rhizopus delemer* lipase, *Rhizopus japonicus* lipase, *Rhizopus niveus* lipase, and Porcine Pancreatic lipase.

When lipase is used, the stabilized lipase structures may, in particular, be used in hydrolysis, acidolysis, alcoholysis, esterification, transesterification, interesterification, ammoniolysis, aminolysis, and perhydrolysis reactions. Other enzyme classes will be used in other reaction mechanisms particular to their function.

More particularly, the emulsion may be provided by dissolving or solubilizing the enzyme in the hydrophilic phase (herein also referred to as 'the water phase' or simply as 'W'), and forming the emulsion by mixing the enzyme containing hydrophilic phase with the hydrophobic phase (herein also referred to as 'the oil phase' or simply as 'O'). Thus, the emulsion may be of the type O/W, ie oil or hydrophobic phase droplets in a continuous water or hydrophilic phase, W/O, ie water or hydrophilic phase droplets in a continuous oil or hydrophobic phase, O/W/O, W/Q/W, or the like.

The process may further include selectively force precipitating the enzyme at the interface (for O/W emulsions) or within the droplet volume (for W/O emulsions), for example, by increasing the concentration of a salt present in the water phase ('salting out').

The cross-linking of the enzyme molecules may be effected by means of a cross-linking agent. Thus, the process may include adding the cross-linking agent to the hydrophilic phase and/or to the hydrophobic phase and/or to the emulsion. The cross-linking agent will typically be selected so that the cross-linking is only effected once a sufficient time period has elapsed, after the emulsion formation, for enzyme orientation at the phase interface to take place.

The cross-linking agent, when used, is a multifunctional reagent, ie a molecule having two or more functional groups or reactive sites which can react with groups on the enzyme to form a cross-linked macromolecule, ie the stabilized structure. The cross-linking agent may be selected from the following: an isocyanate such as hexamethylene diisocyanate or toluene diisocyanate; an aldehyde such as glutaraldehyde, succinaldehyde and glyoxal; an epoxide; an anhydride; or the like. The use of various cross-linking reagents may also allow for modification of the spheres' physical and/or chemical properties.

Protection of the active sites of an enzyme from being occupied by, or reacting with, the crosslinking agent may be achieved by the addition of a temporary protectant that can occupy the active sites during cross-linking. In the case of lipase, this protectant may, for example, be tributyrin. Tributyrin, which is water-soluble, can then easily be removed by washing in water. Specific enzymes (even within specific classes) require different protectants to minimise or prevent activity loss during cross-linking.

If agglomeration of the stabilized enzyme structures or spheres is a problem, this may be reduced or inhibited through the addition of amino acids after cross-linking. These amino acids may react with any residual free cross-linker groups and thus modify the cross-linked spheres' physical properties. Modification of the spheres by amino acids may also enhance the activity of the enzyme towards a specific substrate by manipulating the surface properties of the spheres. Phenylglycine may, for example, be added to cross-linked spheres to improve sphere hydrophobicity while modification with aspartic acid would result in improved hydrophilicity of the spheres.

The process may include recovering or separating the stabilized enzyme structures from the second liquid phase, eg by means of flotation, filtration, centrifugation, magnetism, or the like. The thus recovered stabilized enzyme structures may be washed, if desired, and thereafter dried, if also desired. Drying of the stabilized enzyme structures may be effected by means of spray drying, vacuum drying or lyophilization (freeze drying).

The process may further include, if desired, extracting the first liquid phase from the stabilized enzyme structures, eg by means of drying, freeze drying or extraction with a suitable solvent, such as hexane or supercritical carbon dioxide (for hydrophobic liquids) or water (for hydrophilic liquids). Thus, when it is desired to extract the first liquid phase (normally the oil phase) from the stabilized enzyme capsules, this may be effected by contacting the stabilized enzyme capsules with an organic solvent capable of dissolving the first liquid phase, or by contacting the capsules with a mixture of a suitable surfactant in water. Alternatively, the first liquid phase can then be extracted by supercritical fluid extraction. The fluid is then preferably supercritical carbon dioxide. The critical point for carbon dioxide (31.2° C. and 73.8 bar) is sufficiently low so that the extraction process will not damage the stabilized enzyme structure.

While the hydrophilic phase in which the enzymes are dissolved may comprise only water, it is believed that improved results may be achieved if it then includes a suitable buffer. The buffer should be selected to facilitate the cross-linking of the enzyme molecules, while ensuring enzyme stability. Thus, for example, the hydrophilic phase may comprise a buffer solution with pH 7-8. Such a buffer may be phosphate buffered saline (PBS) solution, a Tris-(hydroxymethyl)-aminomethane (TRIS) buffer-containing aqueous solution, or a $KH_2PO_4$/NaOH solution.

Alternatively, the hydrophilic phase may include or comprise a polyethylene glycol (PEG). When a low molecular weight polyethylene glycol, such as PEG400 or PEG100, is used, it may be used on its own, ie the hydrophilic phase will then consist of the low molecular weight polyethylene glycol. However, a higher molecular weight polyethylene glycol may optionally instead be used, with it then being dissolved in water to form the hydrophilic phase. When an isocyanate is used as the cross-linking agent in a water-in-oil emulsion, the cross-linking agent will react with the PEG as well as with the enzyme, leading to the formation of reinforced stabilized enzyme capsules that contain an enzyme incorporated membrane with an internal hydrogel support. Alternatively, acrylamide may be polymerized to provide a similar support. This can advantageously improve the mechanical strength of the capsules, improving, for example, resistance against shear damage.

The water immiscible phase, ie the hydrophobic phase, may comprise an oil such as mineral, jojoba or avocado oil; a hydrocarbon such as decane, heptane, hexane or isododecane; an ether such as dioctyl ether, diphenyl ether, or the like; an ester such as triglyceride, isopropyl palmitate or isopropyl myristate; or the like. It is believed that the emulsion used in the process of the invention will normally be in the form of a water-in-oil or W/O emulsion; however, as previously indicated, instead a oil-in-water or O/W, oil-in-water-in-oil, ie O/W/O, or water-in-oil-in-water, ie W/O/W, emulsions can be used. Thus, for example, when the enzyme is lipase, a water-in-oil emulsion can be used to ensure that most of the lipase active sites, which are hydrophobic, are oriented outwardly, thus increasing the total effective activity of the structures.

Furthermore, when a water-in-oil emulsion is used, a second enzyme can advantageously be dissolved in the aqueous or hydrophilic phase. If this second enzyme also has the ability to accumulate at the droplet/second liquid phase interfaces, the resultant cross-linked enzyme structures will contain both enzymes. Alternatively, if the second enzyme is selected so that it does not accumulate at the interfaces, a cross-linked enzyme structure will result with one enzyme being a major component of the structure, while the second enzyme is encapsulated or contained inside the structure. Such a combination enzyme structure can advantageously be used, for example, to catalyze multiple reactions in a single reaction step. Moreover, co-factors or reaction mediators, modified or otherwise, may be included in the droplet, e.g. a redox enzyme and suitable mediator may be incorporated in the sphere in order to regenerate a second redox enzyme in the sphere.

In a particular embodiment of the invention, a triglyceride, which is hydrolysable by lipase, may be used as the hydrophobic or oil phase, with an O/W emulsion being formed; the dispersed or oil phase, ie the triglyceride, contained within the stabilized cross-linked structures or spheres is hydrolyzed by the lipase during and after the cross-linking reaction. The hydrolyzed products are generally water-soluble, and can thus readily be leached out, thereby minimizing or reducing the number of processing steps required to produce the stabilized structures.

In yet another embodiment of the invention, an initial O/W emulsion can be formed. In doing so, a certain degree of purification of the lipase takes place, since impurities present therein will not collect at the interfacial boundaries to the same extent as the lipase. The process may then include, before effecting the cross-linking, centrifuging the emulsion and separating a concentrated emulsion from a dilute water phase. Thereafter, a further O/W emulsion can be formed, using the concentrated emulsion. This step can, if desired, be repeated one or more times, to increase lipase purity. After the final such purification step, the emulsion may then be inverted to form a W/O emulsion, by the addition of surfactants with lower HLB values, which may be in the range of 3-10, more preferably 4-6. This ensures preferential orientation of the lipase active sites towards the outside of the dispersed phase droplets. Thereafter, cross-linking of the lipase as hereinbefore described, can be effected.

When an enzyme is used that collects at the interface, and a W/O emulsion is used, the internal cross-linked enzyme sphere morphology can be controlled by modifying the dissolved enzyme concentration in the aqueous phase. For example, a hollow enzyme sphere can be formed through using reduced enzyme concentration, and activity by weight will improve due to decreased average diffusional distances for substrates.

To impart specific properties to the stabilized enzyme structures, a modifier may be added to the hydrophilic phase and/or to the hydrophobic phase and/or to the emulsion. One or more of the following modifiers can be added in this fashion: a surfactant, a precipitator and an additive.

A surfactant may be used when it is desired to impart enhanced enzyme activity (as regards its use in a subsequent catalyzed reaction), and improved emulsion stability. The surfactant may be anionic, cationic, non-ionic, zwitterionic, polymeric, or mixtures of two or more of these. When an anionic surfactant is used, it may be an alkyl sulphate such as sodium lauryl sulphate or sodium laureth sulphate, or an alkyl ether sulphate. When a cationic surfactant is used, it may be centrimonium chloride. When a non-ionic surfactant is used, it may be an ethoxylated alkyl phenol such as polyoxyethylene(10) iso-octylcyclohexyl ether (Triton X100) or polyoxyethylene(9) nonylphenyl ether (Nonoxynol-9). When a zwitterionic or amphiphillic surfactant is used, it may be decyl betaine. When a polymeric surfactant is used, it may be an ethylene oxide-propylene oxide-ethylene oxide triblock copolymer, also known as a poloxamer, such as that available under the trade name Pluronic from BASF, or it may be a propylene oxide-ethylene oxide-propylene oxide triblock copolymer, also known as a meroxapol. A precipitator can be used when it is desired to precipitate the enzyme onto the emulsion interfaces. The precipitator, when present, may be an inorganic salt such as ammonium sulphate; an organic solvent such as 1,2-dimethylethane or acetone; or a dissolved polymer.

Additives or adjuvants will be used to impart desired properties to the emulsion and/or to the stabilized enzyme structures. Properties that can be modified by use of such additives include pH, by using, for example, a buffer; ionic strength, by using, for example, salts; viscosity, by using, for example, PEG; magnetic properties, by using, for example, iron salts; agglomeration tendency, by using, for example, a surfactant possessing steric hindrance properties; and zeta potential, by using, for example, an anionic surfactant.

According to a second aspect of the invention, there is provided an enzyme structure, which comprises cross-linked enzyme molecules so that the structure is stable, with the structure being hollow, and in which the enzymes are immobilized, with a majority of active sites of the enzymes being orientated either internally or externally. The enzyme structure may be as hereinbefore described with reference to the first aspect of the invention.

According to a third aspect of the invention, there is provided a method of carrying out a reaction, which includes allowing a reaction medium to undergo a reaction in the presence of a plurality of the enzyme structures as hereinbefore described, with the reaction thus being catalyzed by the enzyme structures.

The invention will now be described in more detail with reference to the following non-limiting examples and the accompanying drawings.

DETAILED DESCRIPTION OF THE PREFERRED EMBODIMENT

EXAMPLE 1

Non-Optimized

Figure 1:
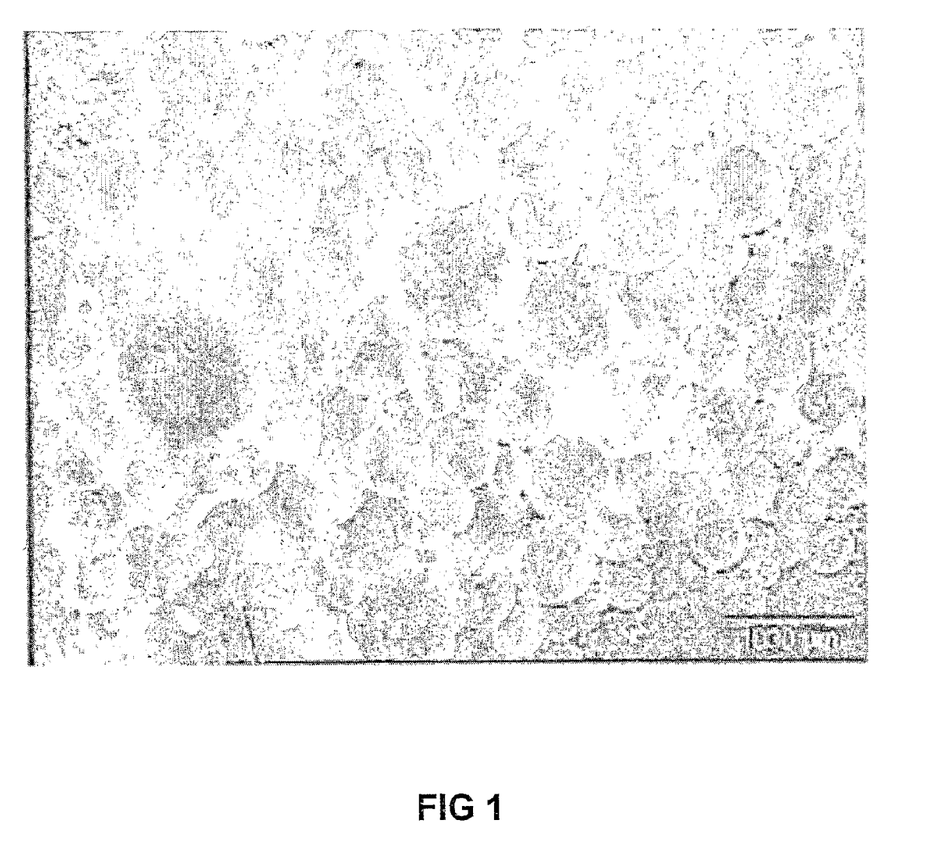
FIG. 1 is an optical microscope picture of cross-linked lipase capsules prepared in accordance with Example 1.
Figure 2:
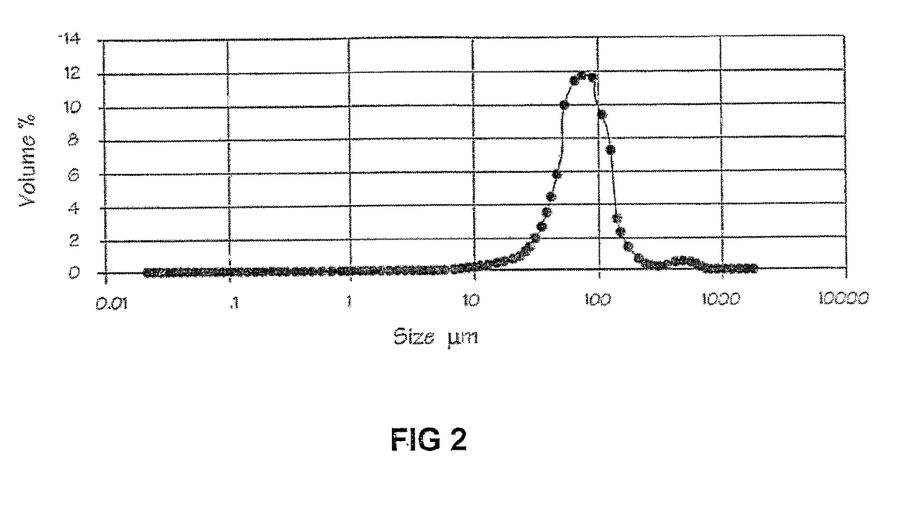
FIG. 2 is a particle size distribution of the cross-linked lipase capsules prepared in Example 1.

Cross-Linked or Stabilized Lipase Spheres (Structures) from Water-in-Oil Emulsion 1 g of lipase Amano AK was added to 195 g phosphate buffered saline (PBS) solution (pH 7.8) and 5 g mineral oil (Castrol). This blend was then homogenized for 5 minutes using a Silverson L4R laboratory rotor-stator homogenizer at 6000 rpm. 1.5 g of hexamethylene di-isocyanate (Merck Schuchardt) was added to the emulsion. The emulsion was then stirred at room temperature for 2 hours. The cross-linked enzyme structures were then recovered by filtration using 0.45 μm filter paper and washed 5 times with 50 ml of PBS each time (total 250 ml PBS). FIG. 1 shows typical stabilized enzyme spheres or structures obtained according to the method. Particle sizes were determined using laser light scattering (Malvern Mastersizer 2000), and an average Sauter mean diameter of 49.4 μm was obtained (see FIG. 2).

The activity of the stabilized enzyme (lipase) structures was determined using a ρ-Nitrophenylacetate assay method as described by Vorderwülbecke, T., Kieslich, K. & Erdmann, H. (1992). 'Comparison of lipases by different assays', Enzyme Microb. Technol., 14, 631-639; and López-Serrano P., Cao L., van Rantwijk & Sheldon R. A. (2002). 'Cross-linked enzyme aggregates with enhanced activity: application to lipases', Biotechnology Letters., 24, 1379-1383.

This assay measures the release of ρ-nitrophenol from a ρ-nitrophenyl ester of a fatty acid. The reaction is done at pH 7.4 at 37° C. and the liberated ρ-nitrophenol is measured at 410 nm. The activity obtained was 63 U/g lipase, where U is μmol/min.

EXAMPLE 2

Cross-Linked or Stabilized Lipase Spheres (Structures) from Water-in-Oil Emulsion A lipase solution was prepared by resuspending *Candida rugosa* lipase (Altus Biologics, Inc.) in 100 mM Tris-Cl (Tris (hydroxymethyl)aminomethane) buffer (pH 8.0) to a final concentration of 100 mg/ml. The enzyme sample was diafiltered using an Amicon ultrafiltration cell fitted with a 10 K polyether sulfone membrane (Microsep (Pty) Ltd, PO Box 391647, Bramley 2018, South Africa) against 3 volumes of 100 mM Tris-Cl buffer (pH 8.0).

Lipase spheres were prepared using the following reagents in the following volumes: 200 μl *Candida rugosa* lipase solution (as prepared above); 50 μl nonoxynol-4; 50 μl tributyrin; 5 ml mineral oil. This mixture was emulsified by stirring for 1 minute at 1500 rpm. To this solution 40 μl gluteraldehyde was added (25% aqueous solution) and allowed to stir for a further 10 minutes. The emulsion was allowed to stand at 4° C. for 12 hours.

Figure 3:
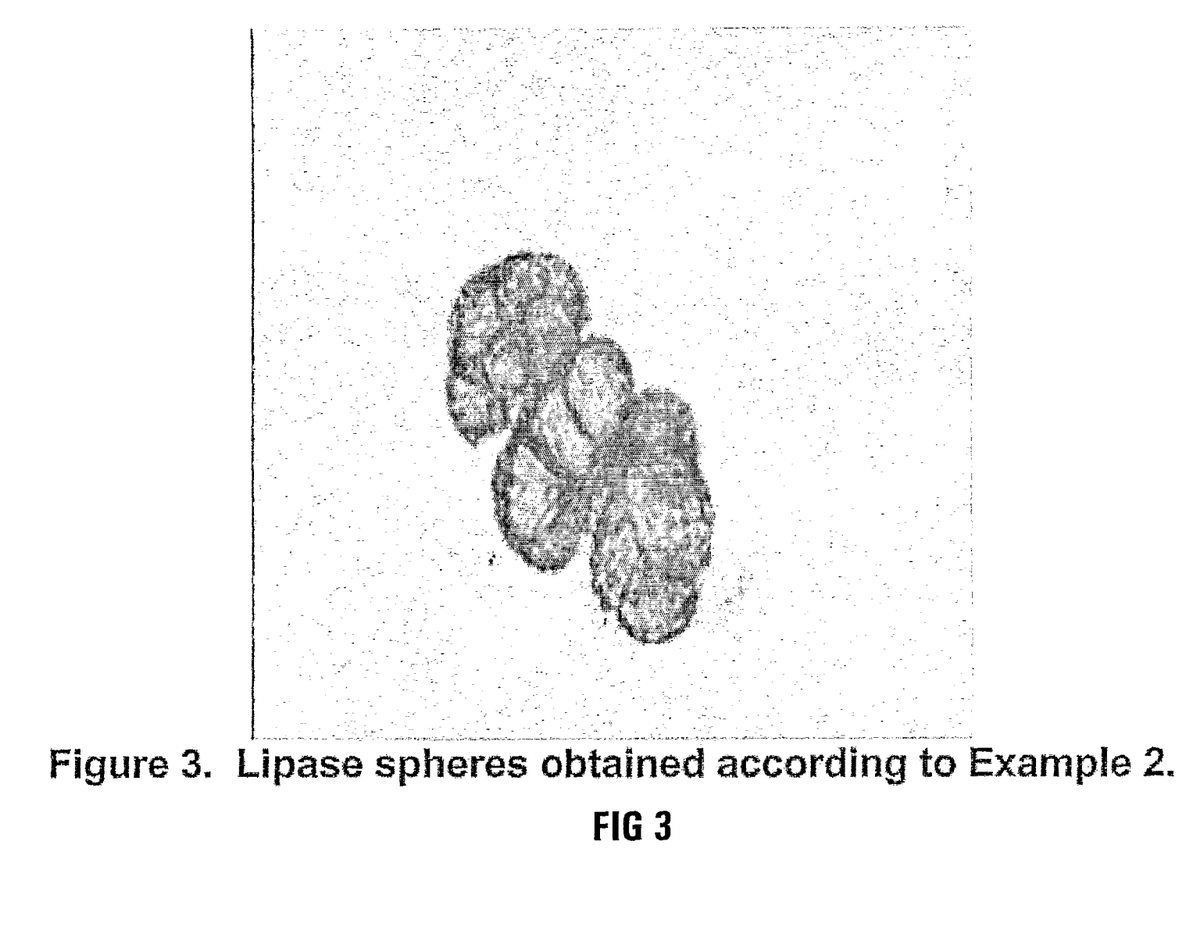
FIG. 3 is an optical microscope picture of cross-linked lipase capsules prepared in accordance with Example 2.
Figure 4:
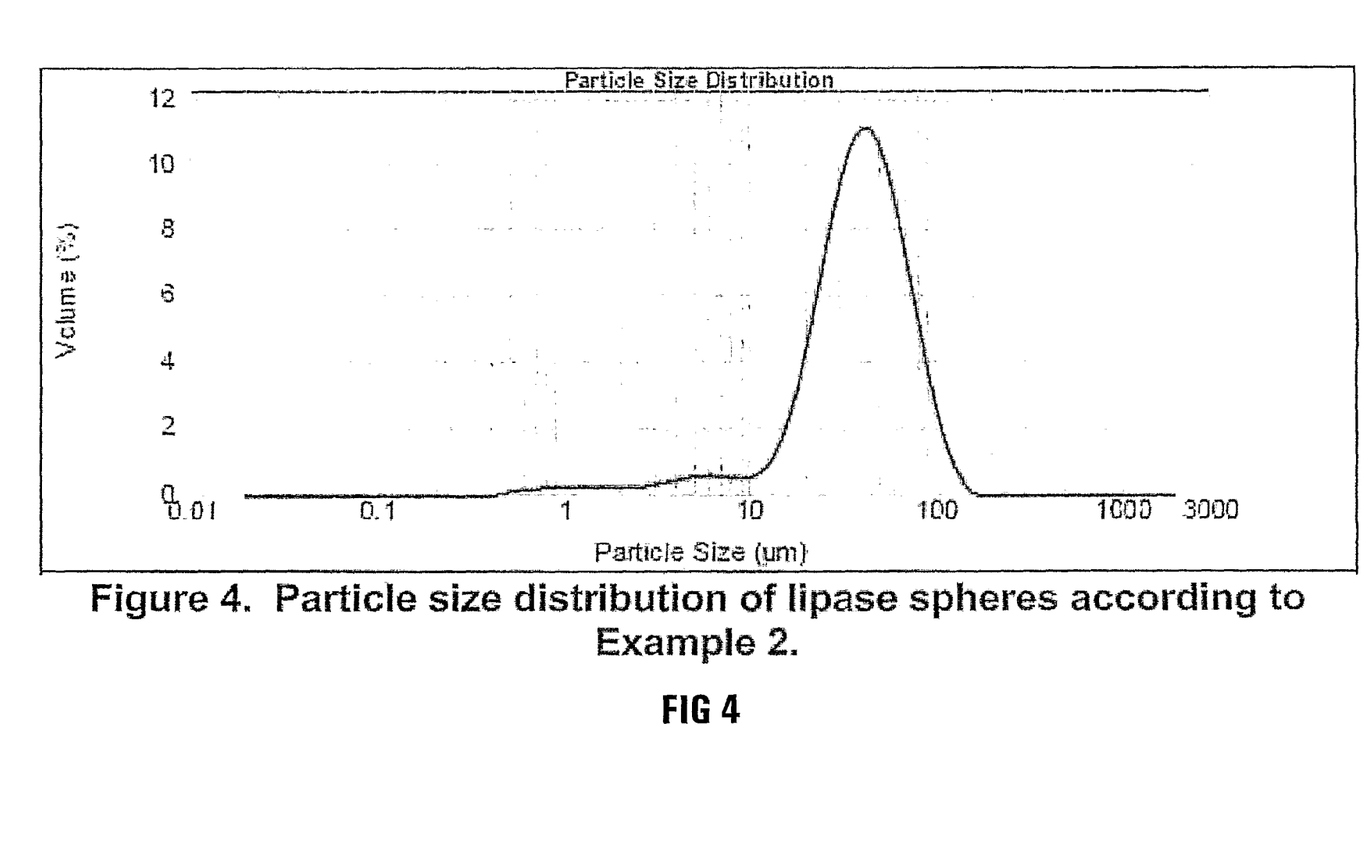
FIG. 4 is a particle size distribution of the cross-linked lipase capsules prepared in Example 2.

After crosslinking the emulsion was centrifuged at 10000 rpm for 5 minutes using a Beckman J2-21 ME centrifuge fitted with JA 20.1 rotor, after which the oil phase was removed. The pellet was washed thrice with 10 ml of 100 mM Tris-Cl buffer (pH 8.0) and pellet was recovered using centrifugation as mentioned above. After washing the pellet was resuspended in 1 ml buffer and assayed for enzyme activity. FIG. 3 shows the enzyme spheres obtained. The spheres had a narrow size distribution between about 10 and 100 μm (FIG. 4).

The activity of the stabilized enzyme (lipase) structures was determined using a ρ-nitrophenylpalmitate and ρ-nitrophenylbutyrate assay method as described by Vorderwülbecke, T., Kieslich, K. & Erdmann, H. (1992). 'Comparison of lipases by different assays', Enzyme Microb. Technol., 14, 631-639; and López-Serrano P., Cao L., van Rantwijk & Sheldon R. A. (2002). 'Cross-linked enzyme aggregates with enhanced activity: application to lipases', Biotechnology Letters., 24, 1379-1383.

This assay measures the release of ρ-nitrophenol from a ρ-nitrophenyl ester of a fatty acid. The reaction is done at pH 8.0 at 37° C. and the liberated ρ-nitrophenol is measured at 410 nm. The activity without tributyrin as additive was 0.11% (for ρ-nitrophenylpalmitate) compared to the original free enzyme in aqueous solution. Surprisingly, the activity obtained with tributyrin as an additive ranged from about 5% (for ρ-nitrophenylpalmitate) to 124% (for ρ-nitrophenylbutyrate) compared to the original free enzyme in aqueous solution.

EXAMPLE 3

Dextran Aldehyde as Cross-Linker

Example 2 was repeated, except that the cross-linking agent used was activated dextran from leuconstoc species, average molecular weight 20 kDa (dextran aldehyde), the oil phase was vegetable oil, the ratio of lipase solution to Tris buffer was 1:1, and no surfactant was used. Dextran aldehyde was prepared by reacting dextran with excess sodium metaperiodate as described by Hong, T., Guo, W., Yuan, H., Li, J., Liu, Y., Ma, L., Bai, Y., & Li, T. (2004) 'Periodate oxidation of nanoscaled magnetic dextran composites', Journal of Magnetism and Magnetic Materials, 269, 95-100. Activity obtained was 7.5% (for ρ-nitrophenylpalmitate) compared to the original free enzyme in aqueous solution.

EXAMPLE 4

Cross-Linked Enzyme Spheres from Oil-in-Water Emulsion

Example 2 was repeated, except that an oil-in-water emulsion was generated by changing the ratio of liquid phases and the surfactant.

EXAMPLE 5

Different Enzyme Class (Laccase)

Example 3 was repeated except that the enzyme used was laccase from UD4 species as described by Jordaan, J., Pletschke, B. I. & Leukes, W. D. (2004) 'Purification and partial characterization of a thermostable laccase from an unidentified basidiomycete'. Enz Microb Technol. 34, 635-641, and the tributyrin was substituted with syringic acid (saturated solution in ethanol).

The spheres were equilibrated with 100 mM succinate-lactate buffer pH 4.5. The spheres were assayed for laccase activity with ABTS as the substrate at 25° C. and the product was followed spectrophotometrically at 420 nm according to the method of Jordaan, J. & Leukes, W. D. (2003) 'Isolation of a thermostable laccase with DMAB and MBTH oxidative coupling activity from a mesophilic white rot fungus'. Enz Microb Technol. 33(2/3), 212-219.

EXAMPLE 6

Protein Concentration

Decreasing the lipase concentration of Example 2 (without tributyrin) by half, leads to an increase of more than 100% in lipase activity by weight.

A possible explanation for the increased activity that was achieved with lower protein concentration (compared to higher protein concentration) is the preferential accumulation of the protein (in this case lipase) at the water-oil interface. This would lead to 'hollow' spheres at lower lipase concentration. On a per weight basis, hollow spheres would be expected to have higher activity compared to 'filled' spheres, due to shorter average diffusional distances for reaction substrates and products.

EXAMPLE 7

Addition of a Precipitant

Addition of acetone as a precipitant to the emulsion of Example 2 (without tributyrin), leads to an increase in activity of 114%.

EXAMPLE 8

Choice of Oil Phase

Substituting vegetable oil for mineral oil in the process of Example 2 (without tributyrin) leads to a four-fold increase in activity, but increased difficulty of recovery from the product solution. This is possibly because of the presence of hydrolysed oil.

EXAMPLE 9

Addition of Protectant

As discussed in Example 2, the addition of tributyrin as protectant, led to an increase in *Candida rugosa* lipase activity from 0.14% to 5% (for $\rho$-nitrophenylpalmitate) compared to the original free enzyme concentration. This 'protectant ability' does not work for all enzymes. For example, the addition of tributyrin as protectant to lipase from *Rhizopus oryzae* led to a twelve-fold decrease in activity from 4.17 to 0.35% (for $\rho$-nitrophenylbutyrate) compared to the original free enzyme.

EXAMPLE 10

Binding of Residual Free Cross-Linker Groups to Reduce Aggregation

Through the addition of an amino acid to the final product, aggregation of spheres was reduced. This is thought to be due to the amino acid binding to the residual crosslinker groups on the sphere surface. Surprisingly, improved activity was also observed compared to controls where an amino acid was not used, specifically when phenylglycine was used as the amino acid. An improvement in activity of about 100% for lipase spheres (based on both $\rho$-nitrophenylbutyrate and $\rho$-nitrophenylpalmitate) was observed compared to the normal method of Example 2 (without tributyrin).

EXAMPLE 11

Recycling of Laccase Cross-Linked Spheres

Laccase spheres were prepared according to the method in Example 5. The spheres were reacted six times with 2,2'-Azino-bis-(3-ethylbenzothiazoline-6-sulfonic acid diammonium salt (ABTS) as a substrate with recovery and washing between each reaction. Laccase activity after these six recycles was comparable to the original activity of the spheres.

EXAMPLE 12

Recycling of Lipase Cross-Linked Spheres with NEE

Lipase spheres were prepared according to the method in Example 2. The spheres were reacted three times with naproxen ethyl ester (NEE) as a substrate at 40° C., with recovery and washing between each reaction. Activity decreased by about 70% over three recycles for the cross-linked lipase spheres (CLECs of the same enzyme showed similar activity losses. Brady, D., Steenkamp, L., Skein, E., Chaplin, J. A. and Reddy, S. (2004) 'Optimisation of the enantioselective biocatalytic hydrolysis of naproxen ethyl ester using ChiroCLEC-CR. Enz. Microb. Technol. 34, 283-291).

EXAMPLE 13

Recycling of Lipase Cross-Linked Spheres with $\rho$-Nitrophenylpalmitate

Lipase spheres were prepared according to the method in Example 2. The spheres were reacted with $\rho$-nitrophenylpalmitate as a substrate, with recovery and washing between each reaction. Activity decreased to 79.6% of original lipase sphere activity in the final recycle.

EXAMPLE 14

Comparison of Lipase Sphere Activity Recovery with CLEA

*Candida rugosa* lipase spheres were prepared according to the method in Example 2. *Candida rugosa* lipase CLEA's were prepared according to Example 8 of United States Patent Application 20030149172, Cao, L., and Elzinga, J., with a gluteraldehyde to ethylene diamine ratio of 1:7.88.

Activity retention of spheres as compared to CLEA's with $\rho$-nitrophenylpalmitate as the substrate was measured as 2.7% for lipase spheres and 3.4% for CLEA's while activity with $\rho$-nitrophenylbutyrate as the substrate was measured as 53.7% for lipase spheres and 6.5% for CLEA's.

EXAMPLE 15

Comparison of Oil in Water and Water in Oil Emulsions (Orientation of Lipase)

Water in Oil *Candida rugosa* lipase spheres were prepared according to the method in Example 2. Oil in Water *Candida rugosa* lipase spheres were prepared according to the method in Example 2 except that the volume of oil was reduced to 0.2 ml and the volume of buffer was increased to 5 ml. Specific activity obtained for the Water in Oil emulsion was 136.0% higher than the Oil in Water emulsion with $\rho$-nitrophenylbutyrate as the substrate, and increase from 8.9 to 26.0 U/mg from the OinW to WinO emulsion.

EXAMPLE 16

Sphere Size Control Effected Through Mechanical Agitation

*Candida rugosa* lipase spheres were prepared according to the method in Example 2, except that a Silverson homogenizer was used to create the emulsion rather than stirring. Two experiments were performed varying only in the speed setting of the homogenizer, namely 1000 and 3000 rpm respectively. Particle size distribution was determined and the results indicated a mean diameter of 52.0 µm and 20.6 µm for the spheres produced using 1000 rpm and 3000 rpm respectively while specific activity increased by 28% and 83% for p-nitrophenylpalmitate and p-nitrophenylbutyrate as substrates respectively compared to.

The invention thus provides a method of stabilizing an enzyme by means of cross-linking, using emulsions as a vehicle therefor. The invention also relates to exposing maximum surface area of enzyme per unit volume of the structure, for subsequent reaction when the structure is used as a catalyst. Additionally, the stabilized enzyme structures are easily recyclable, less expensive than most immobilized enzyme products, and will find widespread application as catalysts in various processes.

Additionally, due to the selective orientation of lipases at the hydrophilic/hydrophobic phase interface, they will be concentrated there. So this method, when applied in the example of an oil in water emulsion, will simultaneously purify the desired lipase from a crude cell lysate. The same would be true of other enzymes with external hydrophobic regions, including many membrane-associated enzymes.

The cross-linking of lipases at the phase interface will fix them in the activated (lid open) state.

The use of oil-in-water emulsions can permit mono-layer lipase spheres, thereby providing a cross-linking method that provides the maximum surface area to enzyme mass.

The use of water-in-oil emulsions would allow for denser, multi-layered enzyme spheres.

This form of enzyme immobilization allows for enzyme recovery and recycling.

It is believed that the process of the present invention, which provides the stabilized enzyme hollow spherical structures, provides the following advantages when the structures are subsequently used to catalyze reactions:
1. Maximum exposed surface area of catalyst (spherical, hollow capsules).
2. Buoyancy of catalyst can be controlled, eg, floating particles could be separated from the reaction medium with ease.
3. The mean size (diameter) of the immobilized enzyme particle formed can be controlled by controlling the size distribution of the emulsion.
4. Through use of the natural self-orientation of many lipases and some other enzymes at solvent interfaces, the immobilized enzyme sphere may be generated in a controlled manner so as to orientate the majority of active sites either towards the lumen or externally as required.
5. Due to the presence of a hydrophilic/hydrophobic interface, enzymes such as lipase are immobilized in the active form.

What is claimed is:

1. A process for producing enzyme particles comprising:
    (a) providing an emulsion of droplets of a first liquid phase dispersed in a second liquid phase, with the one liquid phase being a hydrophilic phase and the other liquid phase being a hydrophobic phase which is immiscible with the hydrophilic phase, and with enzyme molecules being located at or within interfacial boundaries of the droplets and the second liquid phase;
    (b) adding a temporary protectant to the hydrophilic phase and/or to the hydrophobic phase and/or to the emulsion, wherein the temporary protectant occupies active sites of the enzyme, thereby inhibiting occupation of the active sites by a cross-linking agent or reaction of a cross-linking agent with the active sites;
    (c) adding a cross-linking agent to the hydrophilic phase and/or to the hydrophobic phase and/or to the emulsion;
    (d) cross-linking, by means of the cross-linking agent, the enzyme molecules of the respective droplets; and
    (e) recovering the individual enzyme particles from the second liquid phase.

2. The process according to claim 1, wherein the individual particles have openings so that the liquid phases can pass in or out of the particles.

3. The process according to claim 1, wherein individual particles are liquid impervious.

4. The process according to claim 1, further comprising adding to the hydrophilic phase and/or to the hydrophobic phase and/or to the emulsion, a modifier for modifying the hydrophobicity and/or charge of the enzyme, wherein the modifier is selected from the group consisting of;
    (i) a precipitator for precipitating the enzyme onto the emulsion interfaces, (ii) an additive for modifying the pH, ionic strength, viscosity, magnetic properties, agglomeration tendency and/or zeta potential of the emulsion and/or the enzyme particles and (iii) a surfactant.

5. The process according to claim 1, wherein the enzyme is a lipase.

6. The process according to claim 5, wherein the lipase is selected from the group consisting of *Pseudomonas cepacia* lipase, *Pseudomonas fluorescens* lipase, *Pseudomonas alcaligenes* lipase, *Candida rugosa* lipase, *Candida antarctica* lipase A, *Candida antarctica* lipase B, *Candida utiis* lipase, *Thermomyces lanuginosus* lipase, *Rhizomucor miehei* lipase, *Aspergillus niger* lipase, *Aspergillus oryzae* lipase, *Penicillium* sp. lipase, *Mucor javanicus* lipase, *Mucor miehei* lipase, *Rhizopus arrhizus* lipase, *Rhizopus delemer* lipase, *Rhizopus japonicus* lipase, *Rhizopus niveus* lipase, and Porcine Pancreatic lipase.

7. The process according to claim 5, wherein the provision of the emulsion is effected by dissolving the enzyme in the hydrophilic or water (W) phase and forming the emulsion by mixing the enzyme containing hydrophilic phase with the hydrophobic or oil (O) phase.

8. The process according to claim 7, further comprising selectively precipitating the enzyme at the interface when the emulsion is an oil/water (O/W) emulsion in which hydrophobic phase droplets are dispersed in a continuous hydrophilic phase, or within the droplet volume, when the emulsion is a water/oil (W/O) emulsion in which hydrophilic phase droplets are dispersed in a continuous hydrophobic phase.

9. The process according to claim 7, further comprising adding an amino acid to the emulsion to inhibit agglomeration of the individual enzyme particles.

10. The process according to claim 7, further comprising extracting the first liquid phase from the enzyme particles.

11. The process according to claim 7, wherein the hydrophilic phase comprises water.

12. The process according to claim 7, wherein the hydrophilic phase comprises a polyethylene glycol.

13. The process according claim 7, wherein the hydrophobic phase comprises an oil, a hydrocarbon, an ether, or an ester.

14. The process according claim 7, wherein the emulsion is a W/O emulsion in which hydrophilic phase droplets are dispersed in a continuous hydrophobic phase, with a second enzyme, a cofactor and/or a reaction mediator in the hydrophilic phase.

15. The process according to claim 5, wherein a triglyceride, which is hydrolysable by lipase, is used as the hydrophobic phase in an O/W emulsion and wherein the triglyceride is hydrolyzed by the lipase during and after the cross-linking reaction.

16. The process according to claim 7, wherein said process comprises, prior to cross-linking, (1) the formation of an initial emulsion, in which hydrophobic phase droplets are dispersed in a continuous hydrophilic phase, (2) centrifugation of the emulsion and separation of a concentrated emulsion from a dilute hydrophilic phase, to increase lipase purity and (3) the inversion of the emulsion to form a n emulsion in which hydrophilic phase droplets are dispersed in a continuous hydrophobic phase, by the addition of a surfactant with a lower hydrophilic-lipophilic balance (HLB) value.

17. The process according to claim 11, wherein the hydrophilic phase further comprises a buffer in the water.

18. The process according to claim 12, wherein the hydrophilic phase further comprises water admixed with the polyethylene glycol.

* * * * *

UNITED STATES PATENT AND TRADEMARK OFFICE
CERTIFICATE OF CORRECTION

PATENT NO. : 7,700,335 B2
APPLICATION NO. : 10/586894
DATED : April 20, 2010
INVENTOR(S) : Moolman et al.

It is certified that error appears in the above-identified patent and that said Letters Patent is hereby corrected as shown below:

At page 1, item 75, line 1, delete "Dean" and insert therefore, --Sean--.
At page 1, item 75, line 3, after "Avashnee" insert --Shamparkesh--.
At page 1, item 75, line 3, delete "Johannesburg" and insert therefore, --Pretoria--.
At page 1, item 75, line 5, delete "Geriston" and insert therefore, --Germiston--.
At column 3, line 6-7, delete "ammoniolysis," and insert therefore, --ammonolysis,--.
At column 3, line 19, delete "W/Q/W," and insert therefore, --W/O/W,--.
At column 5, line 66, delete "amphiphillic" and insert therefore, --amphiphilic--.
At column 7, line 38, delete "gluteraldehyde" and insert therefore, --glutaraldehyde--.
At column 8, line 10, delete "leuconstoc" and insert therefore, --leuconostoc--.
At column 10, line 8, delete "CR." and insert therefore, --CR.'--.
At column 10, line 32, delete "gluteraldehyde" and insert therefore, --glutaraldehyde--.
At column 12, line 13, in Claim 4, delete "of;" and insert therefore, --of--.
At column 12, line 26 (approx.), in Claim 6, delete "utiis" and insert therefore, --utilis--.
At column 12, line 29 (approx.), in Claim 6, delete "sp." and insert therefore, --sp--.
At column 12, line 55 (approx.), in Claim 13, after "according" insert --to--.
At column 12, line 58, in Claim 14, after "according" insert --to--.
At column 13, line 7 (approx), in Claim 16, delete "a n" and insert therefore, --an--.

Signed and Sealed this

Fourteenth Day of December, 2010

David J. Kappos
*Director of the United States Patent and Trademark Office*